United States Patent [19]
Almeida

[11] Patent Number: 4,942,760
[45] Date of Patent: Jul. 24, 1990

[54] APPARATUS FOR THE MEASUREMENT OF INTERFACIAL TENSION

[75] Inventor: Jaime Almeida, Caracas, Venezuela

[73] Assignee: Intevep, S.A., Venezuela

[21] Appl. No.: 329,581

[22] Filed: Mar. 28, 1989

[51] Int. Cl.[5] .......... G01N 13/02
[52] U.S. Cl. .......... 73/64.4
[58] Field of Search .......... 73/53, 61 R, 64.4

[56] References Cited

U.S. PATENT DOCUMENTS

| | | | |
|---|---|---|---|
| 3,483,737 | 12/1969 | Jennings, Jr. et al. | 73/64.4 |
| 4,050,822 | 9/1977 | Grat | 73/64.4 |
| 4,530,234 | 7/1985 | Gullick et al. | 73/64.4 |
| 4,677,844 | 7/1987 | Sonoda | 73/55 |

*Primary Examiner*—Hezron E. Williams
*Attorney, Agent, or Firm*—Dressler, Goldsmith, Shore, Sutker & Milnamow, Ltd.

[57] ABSTRACT

An apparatus to measure interfacial tension of fluids in equilibrium and, more particularly, a liquid in equilibrium with a gaseous phase thereof using a pendant drop method, at superatmospheric pressure and elevated temeprature conditions. The apparatus includes a visual cell having an interchangeable, multiple capillary injection system, a double-piston pump which permits the drop's injection into the cell without disturbing the experimental conditions, and an optical system comprising a photographic camera, a telemicroscope, and a lighting system.

10 Claims, 3 Drawing Sheets

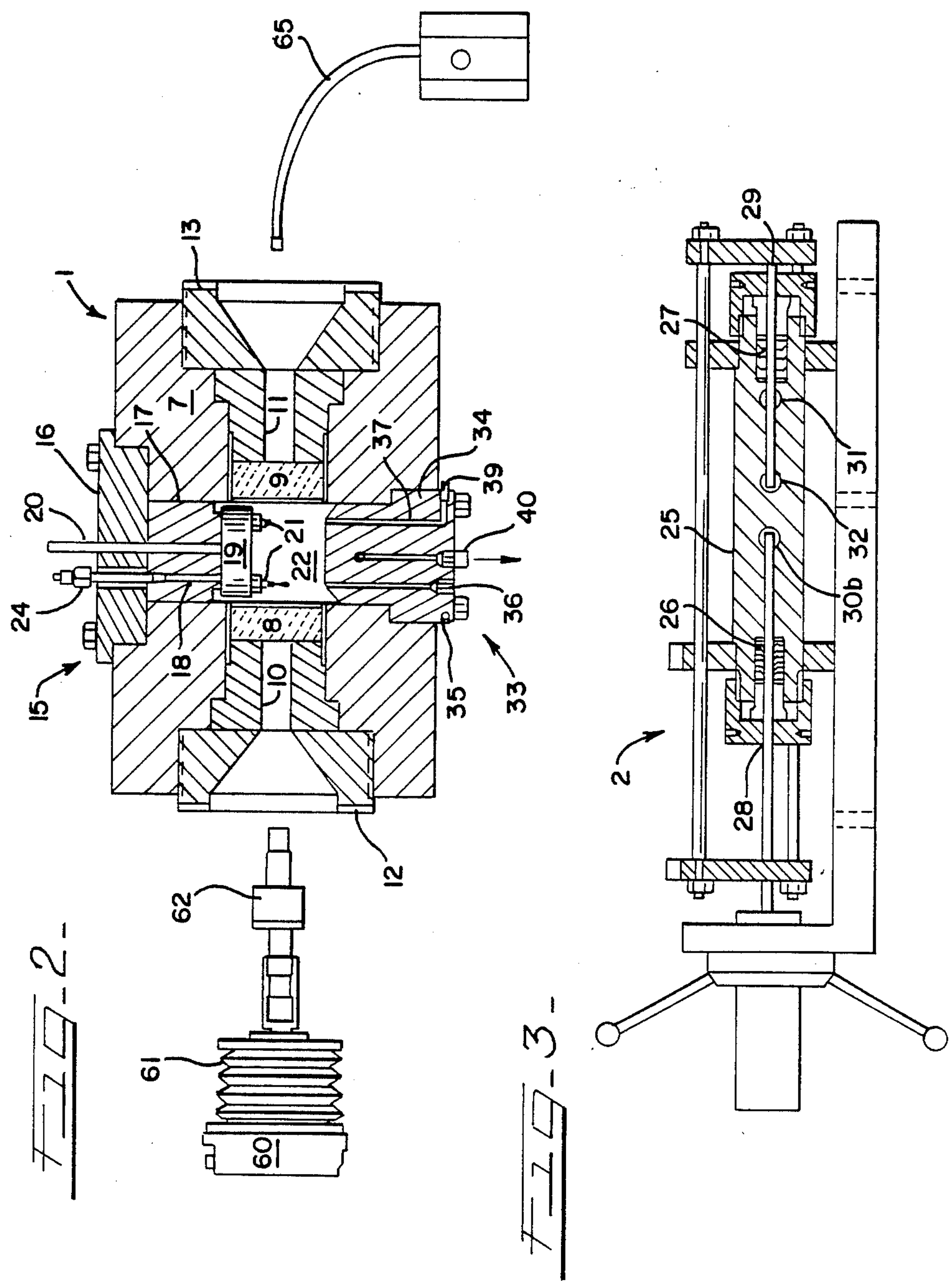
FIG-2-
FIG-3-

APPARATUS FOR THE MEASUREMENT OF INTERFACIAL TENSION

FIELD OF THE INVENTION

This invention relates to apparatus for measuring interfacial tension of fluids such as hydrocarbons or the like.

BACKGROUND OF THE INVENTION

Sophisticated methods based on surface phenomena have been recently developed as mechanisms to recover additional crude organic fuel reserves that could not be recovered through primary production mechanisms. Such processes cannot be duly evaluated if the effects exerted by temperature and pressure on the interfacial tension of hydrocarbons present in a porous medium are not known.

The measurement of interfacial tension at reservoir conditions is useful to determine the interaction that develops at the gas-crude interface and to evaluate how interfacial forces are altered when a chemical additive is added to any phase. Nevertheless, scientists and engineers have been faced for years with the challenge of obtaining a precise measurement of interfacial tension. Among the existing methods to measure the interfacial tension of an equilibrium system the pendant drop method has recently become popular, particularly where it is necessary to measure very low values thereof. This method is based on the formation of a liquid drop on the end of a capillary; the drop outline and the capillary are photographed and the interfacial tension is calculated on the basis of their size and the fluid density under the established experimental conditions.

The apparatus used to obtain the above described data includes a visual cell capable of supporting high pressures and temperatures, and a capillary to form the drop within the cell. In most of the systems previously developed, when a different size drop was to be generated and a different capillary was required, it was necessary to break down the equilibrium conditions within the apparatus by lowering the pressure and temperature in order to uncover the cell and exchange the capillaries. In those operations where relatively high pressures of the order of about 5,000 psia at a temperature of about 300 F were involved, the continual exchange of capillaries represented a serious problem.

In U.S. Pat. No. 3,483,737 to Jennings, Jr. et al., a visual cell is described which includes several capillaries that can be selected to form the drop without varying the pressure and temperature conditions. The capillary selection system in the cell described by Jennings, Jr. et al. is based on internal ring and pinion gears and, preferably, opposed pairs of such gears. That gear arrangement and operation was cumbersome and could pose condensate retention problems which are difficult to control. This, in turn, can considerably affect the gas-liquid interfacial tension measurements for such tension is quite sensitive to impurities. Additionally, there is no provision for precise control of the drop's size, since the drop is controlled through piston-type action exerted by the sample fluid pressure source. Further detailed background information on the equipment and methods heretofore most frequently used to determine interfacial tension can be found in Andreas et al., "The Journal of Physical Chemistry" 42:1001(1938); and Jennings, Jr., "The Review of Scientific Instruments" 28:744–777(1957).

SUMMARY OF THE INVENTION

This invention provides an apparatus for measuring interfacial tension between the gas phase and the liquid phase of a sample fluid through the pendant drop method and, more particularly, for readily measuring the interfacial tension of a liquid in equilibrium with a gaseous phase at various drop sizes and at superatmospheric pressures and elevated temperatures. This is accomplished by a visual cell capable of supporting relatively high pressures and temperatures, and provided with an injection system having several capillaries that can be used in a selective manner without altering pressure and temperature parameters within the cell to form drops of different sizes. Associated with the cell is a double-piston pump which permits a drop-forming fluid phase to be injected while substantially the same volume of a bulk fluid in gas phase, also present within the cell, is extracted from the cell, thereby maintaining a substantially constant pressure within the cell. Recirculating pumps keep both fluid phases moving upstream in order to obtain and maintain a relatively stable equilibrium between both fluid phases.

BRIEF DESCRIPTION OF THE DRAWINGS

In the drawings,

FIG. 2 is a sectional view of the visual cell and associated optical equipment utilized by apparatus embodying this invention;

FIG. 3 is a sectional view of a double-piston pump that forms part of a system embodying the present invention.

DETAILED DESCRIPTION OF THE INVENTION

Figure 1:
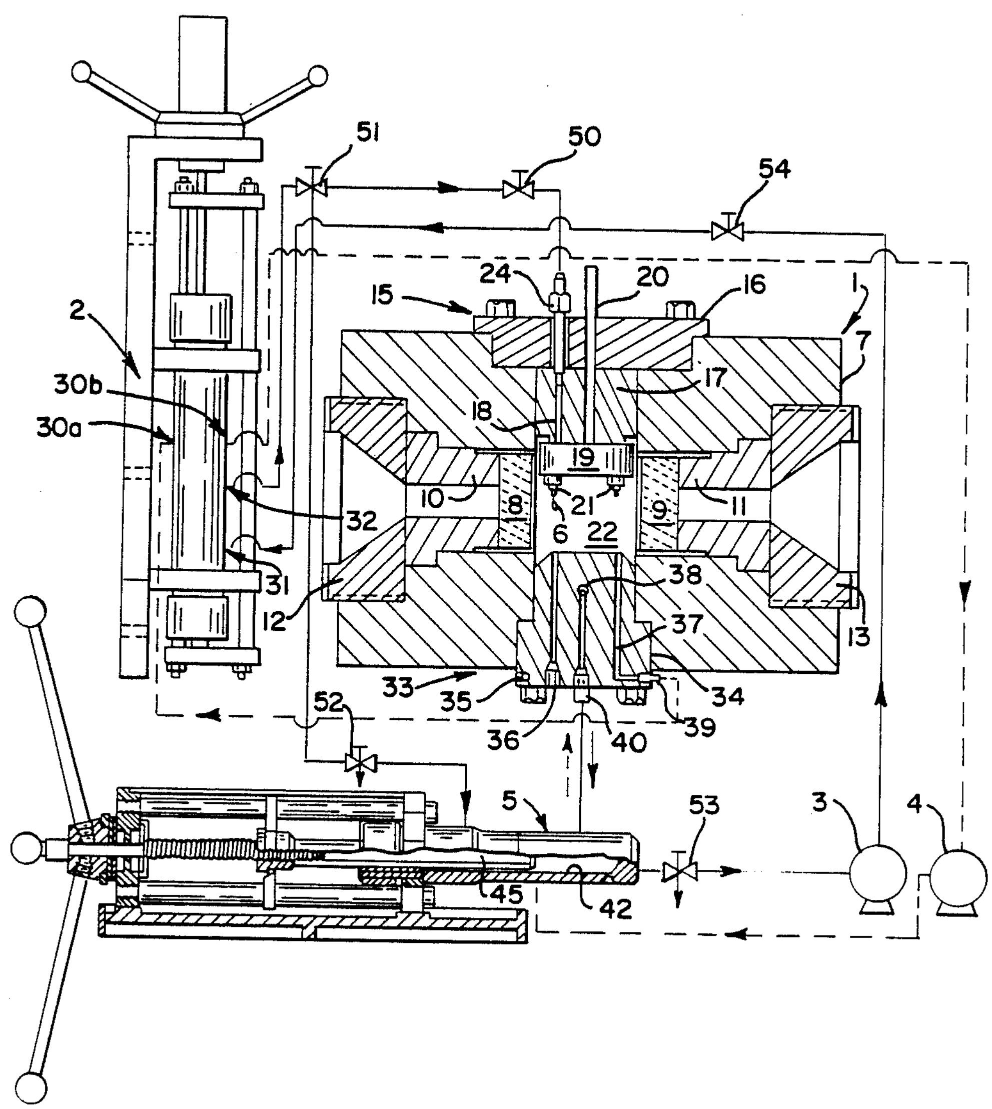
FIG. 1 is a schematic view of apparatus embodying the principles of the present invention.

Apparatus operationally assembled and embodying this invention is shown in FIG. 1. The apparatus comprises a visual cell 1 that defines cavity 22 therewithin, a double-piston pump 2, two recirculating pumps 3 and 4, and an equilibrium chamber defined by housing 5, all of said elements being situated within a controlled-temperature oil bath (not shown). Optical equipment comprising a photographic camera 60 (FIG. 2), a telemicroscope 62 and an optical fiber lamp 65 that provides a lighting system for illuminating a test drop 6 of a drop-forming fluid also form part of the apparatus.

Referring more particularly to FIG. 2, the visual cell 1 is built to support superatmospheric pressures and elevated temperatures, and comprises a cylindrical body 7 containing a pair of opposed optical plane glass windows 8 and 9 which are clamped into stainless steel seats 10 and 11 by means of threaded retainers 12 and 13 that are received in the seats. The superatmospheric pressures can be as high as about 800 atmospheres, and higher, and the elevated temperatures can be as high as about 200 degrees C., and above. The top of the visual cell is closed by drop formation and injection means indicated generally by the numeral 15. Drop injection means 15 comprises a cover plate 16 and a cylindrical sealing member or block 17, said sealing block being fabricated with a liquid sample injection bore 18 extending therethrough. A capillary-bearing turret 19, having a cylindrical configuration, is rotatably mounted in the block 17 in sealing engagement with the bore 18. Turret 19 is rotatable from outside of cell 1 by means of an axle or shaft 20 projecting upwardly from turret 19 and journaled in sealing member or block 17.

The turret 19 carries a plurality of drop forming capillaries 21 spaced from one another and circularly arranged for selective positioning in communication with bore 18. The capillaries 21 terminate in drop-forming tips that are of varying dimension and are adapted to form drops of varying sizes In the embodiment illustrated, five capillaries (only two shown for clarity) are contemplated However, more or less capillaries can be provided, if desired The capillaries 21 depend downwardly from a planar, substantially horizontal face of rotatable turret means 19 and are positioned substantially parallel to one another. Capillaries 21 can also communicate, one at a time, with liquid sample injection bore 18. In such an event, the capillaries are effectively in a fluid-tight relationship with block or member 17. Thus, the passageways defined by each capillary 21, when positioned in communication with bore 18, are effectively sealed against leakage from bore 18. This can be readily seen by reference to FIG. 4.

At the outlet aperture of bore 18 in block 17 is situated a stationary hollow sealing and wiping plug 65 having a through aperture that communicates with bore 18 and can be aligned in registry with the capillary passageway of a selected capillary 21 by rotation of the turret 19. Hollow plug 65 is received in a recess in block 17, and preferably is made of a resilient halogenated hydrocarbon material such as, for example, Teflon, or the like. For enhanced sealing and wiping action, hollow plug 65 is urged radially outwardly by bias means 66 such as an O-ring, or the like. In this manner, the hollow, resilient plug 65 seals against fluid leakage from bore 18, and as the turret is rotated, also provides an effective wiping action against an inner surface of the turret 19 which defines access apertures for the respective capillaries.

Figure 4:
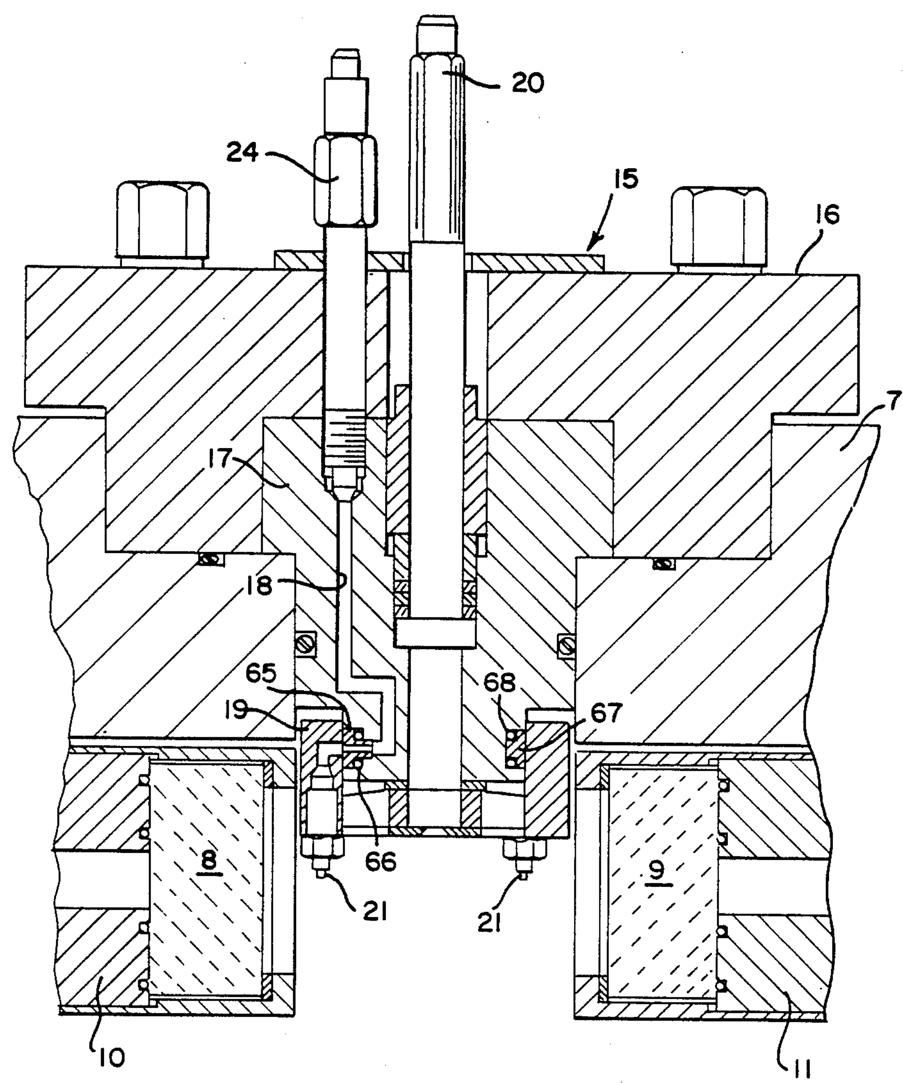
FIG. 4 is a fragmentary enlarged sectional view showing the mounting of capillaries so as to be positionable in communication with the liquid injection bore.

As further illustrated in FIG. 4, an optional solid bearing plug 67 is resiliently seated in another recess in the sealing member 17 and is urged radially outwardly by a resilient O-ring 68, or the like spring or bias means. Preferably, the block 17 carries a plurality of solid bearing plugs 67 (not shown) spaced equally radially from the hollow plug 65 (viz, at 90 degree or 120degree, intervals). The solid bearing plugs 67 serve to substantially equalize the distribution of forces around the turret 19 and, together with hollow plug 65, aid in centering of the turret.

A fitting 24 is fixedly mounted in the cover plate 16 to provide fluid communication between a coacting piston means, such as the double-piston pump 2, and the capillaries 21 in such a manner that the capillaries may be selectively interchanged for formation of a drop 6 without modifying or affecting the equilibrium experimental conditions. The function of the coacting piston means, i.e., double-piston pump 2, is to inject the most dense phase of crude sample without varying the pressure within the visual cell 1. This desirable result is made possible by the withdrawal from the visual cell of substantially the same volume of the least dense phase that is present within cavity 22 of cell 1.

Referring to FIG. 3, the double-piston pump 2 comprises a stainless steel cylinder 25 having opposed bores 26 and 27 carrying coacting pistons 28 and 29. One side of the cylinder 25 (the left side as seen in FIG. 3) has a pair of opposed lateral apertures or ports **30*a* and 30*b* for connection thereto of the conduits that allow circulation of the less dense phase, i.e., the bulk liquid phase, through the system. The cylinder's right side is provided with a pair of longitudinally spaced holes or ports 31 and 32 to recirculate the sample from the denser phase, i.e., the drop-forming liquid. Since both pistons 28 and 29 are mounted on the same support, the functioning principle of the double-piston pump allows equal displacement of both pistons, but in opposite directions, thus withdrawing the same volume from the visual cell cavity 22 as is injected thereinto. As indicated in FIG. 1, the fitting 24 communicates with the port 32 through a pair of valves 50 and 51** whose function will be described hereinbelow.

The bottom of the visual cell 1 is closed by liquid collection means indicated generally by the numeral 33. Liquid collection means 33 comprises a cover member 34 formed with suitable openings 35 and 36 for installation of appropriate temperature and pressure measuring instruments. The cover member 34 is likewise provided with bores 37 and 38 for connection thereto of fittings 39 and 40 for the recirculation of the fluids to be equilibrated. As further seen in FIG. 1, fitting 39 is operationally connected in communication with port **30*a* on the left side of the double-piston pump 2 while the fitting 40 is connected to a conduit operationally connected in communication with equilibrium chamber 42 defined by housing 5. Fitting 40 also communicates with the interior of cavity 22 via bore 38. The volume of the equilibrium chamber is adjustable to modulate the pressure within cavity 22**.

The equilibrium cell 42 communicates with the valve 51 through valve 52, and with the recirculating pump 3 through valve 53. Recirculating pump 3 likewise communicates with the double-piston pump 2 through a valve 54. Each of the valves 51, 52 and 53 is a three-way valve which functions in the manner described hereinbelow.

The camera 60 (FIG. 2) is connected by means of adjustable bellows 61 to a telemicroscope 62 so that the image of the drop 6 can be easily observed. Drop 6 is illuminated by placing a light source 65 at the opposite extreme from the camera 60.

Referring again to FIG. 1, operation of the assembled apparatus for the measurement of interfacial tension according to this invention will now be described. The sample to be studied is introduced through the valve 52 into the equilibrium chamber 42. Pressure in the chamber 42 is modulated or adjusted by means of the volumetric piston 45 in housing 5, which adjusts the size of the equilibrium chamber 42. When the desired conditions of temperature and pressure have been fixed, the sample becomes a two-phase system, i.e., gas and liquid, due to the existing conditions. At that time, the less dense, or gaseous, phase may be recirculated by the recirculating pump 4 through ports **30*a* and 30*b* as well as through cavity 22 which communicates with equilibrium chamber 42 via bore 38. Valves 50, 52 and 53 are closed at this time, valves 51 and 54 are open, and recirculating pump 3 causes the more dense fluid to follow the circuit indicated, through ports 31 and 32 as well as through chamber 42. During this step, the more dense fluid goes from the chamber in double piston pump 2 to the equilibrium chamber 42 through valves 51 and 52, because valve 50 is closed, thereby preventing recirculation through the capillary 21. The less dense fluid is taken from the cavity 22 through fitting 39 and bore 37, it goes through ports 30***a* and 30*b* of the double piston pump 2 and then is pumped to equilibrium chamber 42. Recirculation is now stopped, and valves 51 and 54 are closed. To form the drop 6 in cavity 22, valve 50 is opened, and the denser, drop forming fluid is injected with the double piston pump 2, which simultaneously withdraws the same volume of the less dense fluid from the visual cell 1. Once the drop 6 has been formed, it is illuminated with the light source 65, and a picture is taken with the camera 60 for further analysis and study. If the size of the drop is not adequate because it is either too large or too small, or if a different drop size is desired for comparison, the capillary is exchanged for another by rotating the shaft 20 while predetermined pressure is maintained within cavity 22 of the cell. When the shaft 20 rotates, the capillary 21 that was in registry with the bore 18 is replaced by another capillary of different diameter without disturbance of the desired experimental conditions within the cell. The resilient plug 65 prevents leakage and wipes the turret 19 clean during such rotation.

It will be appreciated from the foregoing detailed description of the invention and the illustrative embodiment thereof that numerous variations and modifications may be effected without departing from the true spirit and scope of the novel concept of the principles of the invention.

What is claimed is:

1. An apparatus for measuring interfacial tension between a gas phase and a liquid phase of a fluid by the pendant drop method comprising:

a visual cell defining a cavity capable of supporting high pressures and temperatures;

plural drop forming means in said cell for forming drops of various sized and comprising a plurality of capillaries of varying sizes positioned within said cavity together with selective positioning means actuatable from outside of said cell for selectively positioning any of said capillaries into fluid-tight communication with an injection means for introducing a drop of the liquid phase into capillary positioned in registry therewith while maintaining existing superatmospheric pressure within the cell; said selective positioning means comprising a substantially horizontal capillary-bearing turret rotatably mounted in said cell, wherein said capillaries are spaced from one another and circularly arranged on said turret substantially parallel to one another, and a shaft secured to said turret and projecting out of said cell and operable to rotate said turret;

recirculation means for recirculating the fluid phases through the cell; and means for modulating the pressure within the cell.

2. The apparatus according to claim 1 wherein a hollow plug defining a through passageway is resiliently mounted between the injection means and the turret to provide sealing but communicating engagement of said injection means with any one of said capillaries and to wipe said turret free of injected liquid phase when said turret is rotated.

3. An apparatus for measuring interfacial tension between a gas phase and a liquid phase of a fluid by the pendant drop method comprising:

a visual cell defining a cavity capable of supporting high pressures and temperatures;

plural drop forming means in said cell for forming drops of various sizes;

injection means for introducing a drop of the liquid phase into a plurality of said drop forming means while maintaining existing superatmospheric pressure within the cell, said injection means including a coacting piston means for simultaneously injecting a drop of liquid phase into said cell while withdrawing an equal volume of gas phase therefrom;

recirculation means for recirculating the fluid phases through the cell; and means for modulating the pressure within the cell.

4. The apparatus according to claim 3 wherein said coacting piston means comprises a double-piston pump operationally connected to communicate with the cavity defined by said cell.

5. The apparatus according to claim 3 wherein said modulating means comprises a movable piston in fluid communication with the cavity of said cell and adapted to define an equilibrium chamber of predetermined volume for the apparatus, and manually operable pressure adjusting means associated with said movable piston for adjusting equilibrium pressure within said cavity.

6. The apparatus according to claim 5 wherein said recirculation means comprises a pair of recirculating pumps in fluid communication with said equilibrium chamber and said injection means.

7. In an apparatus for measuring interfacial tension between a less dense and a more dense fluid by pendant drop method and including a visual cell defining a cavity capable of supporting superatmospheric pressures and elevated temperatures, means for infusing the cell with a less dense fluid and introducing means for injecting a drop of a more dense fluid into the cell, a drop forming means that comprises:

a capillary-bearing turret rotatably mounted in said cell at the top thereof and positioned within said cavity;

a plurality of capillaries mounted on said turret with their respective drop-forming tips depending downwardly therefrom, said capillaries having varying dimensions and being adapted to form drops of various sizes;

means for rotating said turret to selectively position each of said capillaries in operational fluid communication with said injection means while maintaining a predetermined pressure within said cell;

a hollow plug having a through passageway mounted between said injection means and said capillary turret; and a resilient O-ring urging said plug against the turret to provide fluid tight communication with any of said capillaries and to wipe said turret free of fluid when the turret is rotated.

8. Apparatus according to claim 7 wherein said injection means comprises a cylindrical sealing member having an injection bore formed therein, said member having the hollow sealing plug received in a recess in said sealing member and communicating with said bore.

9. Apparatus according to claim 8 further including a solid bearing plug resiliently mounted in a recess in said sealing member and spaced peripherally from said hollow sealing plug.

10. Apparatus according to claim 8 wherein said means for rotating the turret comprises a shaft journaled in said sealing member, rigidly connected to said turret, and projecting out of said cell through said sealing member and operable to rotate said turret.

* * * * *